(12) United States Patent
Hillion et al.

(10) Patent No.: US 6,221,920 B1
(45) Date of Patent: Apr. 24, 2001

(54) COMPOSITION THAT CAN BE USED AS AN EMULSIFYING AND DISPERSING SURFACE AGENT AND ITS PRODUCTION PROCESS

(75) Inventors: Gérard Hillion, Herblay; Isabelle Durand, Rueil Malmaison; Robert Stern, Conflans Sainte Honorine; Marie Velly, Montesson, all of (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 0 days.

(21) Appl. No.: 09/160,290

(22) Filed: Sep. 25, 1998

(30) Foreign Application Priority Data

Sep. 25, 1997 (FR) .................................. 97 12049

(51) Int. Cl.$^7$ ................................ B01F 3/04; B01F 3/08; B01F 17/22
(52) U.S. Cl. .............................. 516/15; 516/27; 516/31; 516/33; 516/69; 516/915; 554/66
(58) Field of Search ............................... 516/27, 69, 915, 516/33, 31, 15; 510/502; 554/66, 25; 44/418

(56) References Cited

U.S. PATENT DOCUMENTS

| 2,002,613 | * | 5/1935 | Orthner et al. .................. 510/502 X |
| 2,566,515 | * | 9/1951 | Danforth .............................. 554/25 X |
| 3,244,638 | * | 4/1966 | Foley et al. ............................ 516/27 |
| 3,395,162 |   | 7/1968 | Lamberti . |
| 3,515,754 | * | 6/1970 | Mod et al. ......................... 554/66 X |
| 3,903,410 | * | 9/1975 | Akrongold et al. ............. 510/502 X |
| 4,108,779 |   | 8/1978 | Carney . |

FOREIGN PATENT DOCUMENTS

| 543960 | | 1/1956 | (BE) . |
| 420545 | * | 11/1934 | (GB) ..................................... 554/66 |

* cited by examiner

*Primary Examiner*—Richard D. Lovering
(74) *Attorney, Agent, or Firm*—Millen, White, Zelano & Branigan, P.C.

(57) ABSTRACT

The following are described herein: a composition that consists of a mixture that comprises at least amides, amines, ester-amides, ester-amines, amine salts and monoglycerides, that are all derived from monomeric, dimeric, trimeric and/or tetrameric fatty acids; a process for the production of said composition which comprises the transamidification reaction of a polyunsaturated vegetable oil that is polymerized thermally, with an excess of at least one amino alcohol, which may or may not be in the presence of a catalyst; and the uses of this composition particularly as an emulsifying agent that allow it, depending on the nature of the oil, to form an oil-in-water or water-in-oil emulsion, as a solid-dispersing agent, or as an agent for the stabilization of foams in a liquid or an emulsion.

25 Claims, No Drawings

COMPOSITION THAT CAN BE USED AS AN EMULSIFYING AND DISPERSING SURFACE AGENT AND ITS PRODUCTION PROCESS

The object of the invention is a composition that consists of a mixture that comprises at least amides, amines, ester-amides, ester-amines, amine salts, and monoglycerides that are all derived from monomeric, dimeric, trimeric, and/or tetrameric acids and a process for the production of said composition, which comprises the reaction for transamidification of a polymerized polyunsaturated oil, with an amino alcohol.

The invention also relates to the uses of this composition, particularly as an emulsifying agent, that make it possible, depending on the nature of the oil, to form an oil-in-water or water-in-oil emulsion, as an agent for dispersing solids, or as an agent for stabilizing foams in a liquid or an emulsion.

The mixture that is obtained can be used, without any purification, as an emulsifying and dispersing surface agent, in the pure state, or after dilution with various solvents such as, for example, aromatic fractions, various alcohols, or else with certain fatty acid esters.

It is known that the products that are obtained from the amidification of a mixture of fatty acid oligomers with, for example, diethanolamine, have advantageous emulsifying and dispersing properties in various applications for forming water-in-oil or oil-in-water emulsions, depending on the nature of the oil that is used and the respective proportions of these two components.

Furthermore, the articles by D. N. Bhattacharyya et al. (J. Surface Sci. Technol., Vol. 5, No. 2, pp. 187–189, 1989, and Tenside Surf. Det. 27, 5, pp. 307–311, 1990) describe the preparation of ethanolamides by reacting diethanolamine on "bodied oils" after saponification or transesterification in the form of methyl esters of oils that are polymerized thermally.

It has now been found, surprisingly enough, that it was possible to obtain, in a simple and economical manner, a product that has the same surfactant properties as the alkanolamides of standard dimers by using another source of fatty acid oligomers, and this is to directly use oils that are polymerized thermally.

The object of the invention lies in the fact that there is obtained, in a single stage, a product that is very inexpensive and that corresponds to certain surfactant characteristics, including a pronounced amphiphilic nature that makes it possible to produce water-in-oil or oil-in-water emulsions.

The elimination of several major stages such as:
- standard dimerization, with activated earths, ion-exchange resins, or sulfonic acids, followed by the elimination of these catalysts;
- the amidification of the fatty acid oligomers with the elimination of reaction water; and finally
- the elimination by filtration of an insoluble reaction by-product that comes from the dehydration reaction of two diethanolamine molecules (when this amino alcohol is used), which provides the N,N-bis(2-hydroxyethyl) piperazine, makes it possible to reduce the synthesis time by a factor of 5 to 6.

Actually, by going the way of standard synthesis, a mean reaction time on the order of about 15 hours is generally obtained, while when the process steps of the invention are used, a total mean time of three hours is adequate.

It is known that polyunsaturated oils that are rich more particularly in dienic or trienic fatty acids are polymerized by the action of heat to form polymeric structures that are called "stand oil," "standolie," "bodied oil," or, in the specific case of linseed oil, linseed oil that is thickened by heating.

This thermal polymerization can be carried out only by putting into contact with one another dienic or trienic fatty chains, such as, for example, linoleic acid and linolenic acid.

This reaction is obtained by simple thermal heating at 300° C. under nitrogen, or at 280–290° C. under reduced pressure in the presence of anthraquinone or benzoquinone (see Nisshin Oils Mills, Yokohama, Japan, Nagakura and Coll. (1975), 48 (4), 217–22) or also catalyzed by metals such as, for example, zinc, lead, tin, or copper, in the form of nitrates, chlorides, stearates, etc.

It is possible to cite as an example: heating of linseed oil with 0.5 to 2% of copper (II) nitrate for 6 hours [see Sil, S. and Koley, S. N., Department of Chemical Technology, Univ. of Calcutta (1987) 37 (8), 15–22].

The heating time depends on a viscosity gradient with polymerized linseed oil which can reach, after a heating period of more than 20 hours, a viscosity of 65 Pa.s at 20° C.

Aside from linseed oil, it is possible to obtain polymerized oils by using sunflower seed oil, safflower oil, china wood oil, grapeseed oil, soybean oil, and corn oil, as well as all the oils that have high contents of linoleic acid and/or linolenic acid.

Given below, by way of example, is the composition of fatty acid oligomers that are contained in a polymerized linseed oil that has a viscosity of 65 Pa.s at 20° C.:

monomeric fatty acids=44.10%,
dimeric fatty acids=32.30%,
trimeric fatty acids=14.50% and
high-grade oligomers=9.10%.

These values were obtained after methanolysis of the triglyceride, and their separation was done by gel permeation chromatography (GPC). The acid index of the polymerized oil is equal to 16 mg of KOH/g.

The other way of producing fatty acid dimers uses activated earths. It is possible to cite, for example, U.S. Pat. Nos. 2,347,562, 2,426,489, and 2,793,220. This approach consists in dimerizing, at a temperature of 210–230° C., oleic acids or linoleic acids in the presence of an activated earth of the family of aluminosilicates of alkaline metals and alkaline-earth metals, such as, for example, montmorillonite, sepiolite, attapulgite, or halloysite.

By using the "Emery" process from the Unilever Company (described in, for example, U.S. Pat. No. 2,835,430), a product is obtained, for example after reaction, that contains about 55% by weight of dimers and trimers of fatty acids, whereby the remainder consists mainly of stearic acid and isostearic acid, and whereby the latter consists of a mixture of products that results from the skeletal isomerization of the fatty acid molecule.

The reaction product should then be purified by distillation to eliminate the fraction of monomeric acids. Then, a mixture is obtained whose composition is on the order of 1% monomeric acids, 75% dimeric acids, 19% trimeric acids, and 5% high-grade oligomers.

It is also possible to cite the catalysis by sulfonic acids described in, for example, U.S. Pat. No. 4,391,258 from the Unilever Company, as well as by strongly acidic ion-exchange ions (see Patent Document DE-A-3 250 470 by Henkel GmbH).

Note that these various methods can be used both on the fatty acids and on their corresponding esters (for example, in the form of methyl esters, ethyl esters, propyl esters, butyl esters, etc.)

The amidification reaction of the fatty acids by a primary or secondary amine is known in the prior art and operates between 110 and 160° C. without a catalyst with elimination of water as it forms, either by using a third solvent to obtain an azeotrope or by operation without a solvent, but by elimination of water by distillation under reduced pressure (see, for example, U.S. Pat. No. 2,089,212 and the article by Harry Kroll and Herbert Nadeau in J.A.O.C.S. 34, 323–326, June 1957).

The originality of the invention lies in the fact that as a dimer source, a polymerized oil that has a viscosity of between 5 and 65 Pa.s and that is made to react with excess amino alcohol is used.

The amino alcohols that can be used are, for example, monoethanolamine, monopropanolamine, monoisopropanolamine, 1-amino-butanol, 2-amino-1-butanol, N-methylethanolamine, N-butylethanolamine, pentanolamine, hexanolamine, cyclohexanolamine, polyalcohol amines, or else polyalkoxyglycolamines, as well as amino polyols such as diethanolamine, diisopropanolamine or trihydroxymethylaminomethane. Preferably, diethanolamine will be used.

The reaction is generally carried out in the absence of a solvent and catalyst, under a nitrogen atmosphere and at a temperature that is between 100 and 200° C. and preferably at a temperature of 160° C. The reaction can also be catalyzed, however, which appreciably reduces the reaction time. Generally alkaline alcoholates such as methylate or ethylate of lithium, sodium, or potassium are used. The reaction time is then 15 to 200 minutes; preferably the reaction is halted after 100 minutes.

The polymerized vegetable oils that can be used should have a viscosity of 5 to 65 Pa.s at 20° C. and preferably 10 to 20 Pa.s. They generally have an acid index of between 8 and 20.

The molar ratio of the amino alcohol to the polymerized oil, relative to the moles of fatty acids that are contained in the oil, should be 1 to 2 and preferably on the order of 1.5.

The product that is obtained can be used directly without any purification, either in the pure state or after dilution in a solvent that is suitable for the emulsifying application that is selected. The compatible solvents that can be used can be selected from among the aromatic solvents, such as, for example, toluene or xylenes, aromatic solvent fractions; monoalcohols, such as, for example, methanol, ethanol, propanol, isopropanol, butanol, isobutanol or dodecanol, monopropylene glycol diols, and diethylene glycol diols; all C1 to C4 monoalcohol esters and C6 to C22 fatty acids, such as, for example, those that are derived from vegetable or animal oils or fats, as well as the same pure esters, such as, for example, methyl or ethyl hexanoate and octoate.

The C1 to C4 monoalcohol esters and C6 to C22 fatty acids that are derived from vegetable or animal oils or fats can be selected from among, for example, the methyl and ethyl esters of the oils of copra, babassu, palm nut, tucum, murumuru, palm, karite, olive, peanut, kapok, bitter date, papaya, colocynth, croton, cypress grass, purging, hemp, beech, hibiscus, physic nut, cameline, safflower, niger, sunflower seed, oleic sunflower seed, rubber, coconut, purga, nut, corn, soybean, cotton, sorghum, grapeseed, linseed, tobacco, common wood turpentine, afzelia, turnip, mustard, brown mustard, china wood, bankul, aleurite, amoora, spruce, cramble, perilla, erucic colza, new colza, oleic colza, sesame, cocoa butter, tall oil, wheat and ricin; and those among the methyl and ethyl esters of fats such as lard, tallow, and melted butter, as well as fish oils, as is or partially hydrogenated.

In some applications where it is possible to have contact with the environment, the use of aromatic solvents should be replaced by solvents that are non-toxic and have a certain biodegradability, and hence it is advantageous to use as solvents fatty esters that are obtained from vegetable bases, such as, for example, methyl or ethyl ester of colza oil.

The compositions that are defined in the invention can have a large number of applications. They can be used as emulsifying agents that allow, depending on the nature of the oil, oil-in-water or water-in-oil emulsions to be formed. They can also be used as solid-dispersing agents or as foam stabilizers in a liquid or in an emulsion.

A special use consists in forming stable ice dispersions in media that contain hydrocarbon, for example in light petroleum condensates.

The entire disclosure of all applications, patents and publications, cited above and below and of corresponding French Application 97/12049, filed on Sep. 25, 1997, are hereby incorporated by reference.

The following examples illustrate the invention but should in no way be construed as limiting. Examples 2, 3, and 4 are given by way of comparison.

EXAMPLE 1

In a one-liter flask that is equipped with mechanical stirring and heated by an oil bath, 325 g of polymerized linseed oil (0.37 mol), computed in triglyceride equivalent and having a viscosity of 10 Pa.s at 20° C. with 175 g of diethanolamine (1.66 mol), is introduced under a nitrogen atmosphere.

The corresponding composition in terms of fatty acids and fatty acid oligomers of this polymerized linseed oil is as follows:

monomeric fatty acids=48.8%, dimeric fatty acids=31.4%, trimeric fatty acids=13.0% and high-grade oligomers=5.8%.

The acid index of the product is equal to 10.

The mixture is heated to 160° C. After being reacted for 15 to 20 minutes at 160° C., the product becomes homogeneous and clear. This temperature of 160° C. is held for 100 minutes before the mixture is cooled.

The dilution of the product is done in the reaction flask by introducing 500 g of an aromatic fraction whose distillation interval is between 180 and 215° C.

The mixture that is thus obtained is a yellow liquid with a density at 25° C. of 950 kg/m$^3$, a viscosity at 20° C. of 0.212 Pa.s, a flash point >60° C., and a flow point <20° C.

The total time of this synthesis, taking into account the heating times, is between 2 and 3 hours.

EXAMPLE 2 (COMPARATIVE)

Introduced into the same equipment as for Example 1 is 330 g of a mixture of fatty acids that come from a sunflower seed oil, whose composition is as follows:

palmitic acid=6%, stearic acid=5%, oleic acid=18%, linoleic acid=69%, and 35 cm$^3$ of a strongly acidic ion-exchange resin of the sulfonic, predried type (Amberlyst 15® resin).

Under a nitrogen atmosphere, this mixture is gradually heated to 130° C. while stirring is continued.

After 7 to 8 hours of reaction at 130° C., the conversion into fatty acid oligomers is 54.5% (according to the analysis that is obtained by GPC).

After the ion-exchange resin is filtered, 295 g of a mixture of monomeric, dimeric, and trimeric fatty acids, whose acid index is equal to 195, is recovered. This corresponds to 1.026 mol of fatty acidity. Into this mixture is introduced 1.54 mol of diethanolamine, or 161.6 g, and it is gradually heated to a temperature of 160° C. As soon as the temperature of 130° C. is reached, the operation of putting the equipment under vacuum is initiated to facilitate eliminating the water reaction until, at the end of the reaction, a vacuum on the order of 50 to 60 mm of mercury is obtained. After 7 hours of reaction, 29 g of water that contains 2.1 g of diethanolamine has been recovered.

The composition of the reaction mixture is determined by assay. 1.18 mol of total amine, 0.8 mol of free diethanolamine, 0.38 mol of amino-esters, approximately 0.02 mol of amine salts, and on the order of 2.2 mol of amides, per kilogram of product produced, are found.

The residual acidity of the product corresponds to an acid index on the order of 1. The dilution of the reaction product is done by adding 422 g of the solvent that is used in Example 1, consisting of a fraction of aromatic solvents.

After a storage period of 72 hours, the appearance, in the diluted product, of small white crystals is noted. The analysis of this solid, by combining chromatography and mass spectrometry, shows that this is N,N'-bis (2-hydroxyethyl) piperazine. This product results from the dehydration of two diethanolamine molecules. Gas chromatography assay makes it possible to estimate the amount of this by-product in the undiluted product at 3% by weight.

The total time for this synthesis, including the heating time and the filtration stage, is on the order of 18 hours.

EXAMPLE 3 (COMPARATIVE)

Into a 0.5 liter stainless-steel pressurized reactor are introduced 350 g of commercial oleic acid (whose oleic acid content is approximately 65% and whose total of unsaturated fatty acids with 18 carbon atoms is on the order of 80%) and 35 g of activated earth of the montmorillonite type (Tonsil Optimum FF®).

This mixture is heated while being stirred under a nitrogen atmosphere, and the temperature is raised until it reaches 230° C. After 5 hours at 230° C., GPC analysis shows that approximately 55% of a mixture of fatty acid dimers and trimers and 45% of monomeric acids that contain 25% palmitic and stearic acids and approximately 20% of a mixture of more or less saturated branched fatty acid isomers are produced.

After the activated earth is filtered on a paper filter, 308 g of the product which will be amidified by diethanolamine, following the same procedure as for Example 2, is recovered.

170.8 g of diethanolamine (1.63 mol) is added, and after 6 hours of reaction, 30 g of water that contains 2.3 g of diethanolamine is recovered. The residual acid index is equal to 1.4 mg of KOH/g of product, and the content of N,N'-bis (2-hydroxyethyl) piperazine that is obtained by chromatographic analysis is 2.8%. 448 g of product that can be used directly as is or after dilution that is aimed at appreciably reducing viscosity so that it can be handled easily is recovered in fine.

The reaction time that was necessary for obtaining the product was approximately 15 hours.

EXAMPLE 4 (COMPARATIVE)

345 g of sunflower seed oil methyl esters with a composition that is identical to that of the fatty acid mixture used in Example 2 and 35 cm$^3$ of strongly acidic ion-exchange resin (Amberlyst 15®) are introduced, and it is gradually heated to 130° C. under a nitrogen atmosphere. After 6 hours of reaction, an oligomer conversion rate (dimers+trimers) of 56% according to GPC analysis is obtained.

After the resin is filtered, 310 g of product to which 162 g of diethanolamine is added is recovered.

It should be noted that the amidification of an ester, unlike that of an acid, should be catalyzed. Catalysis by an alkaline alcoholate is done most often.

The mixture is therefore heated, and as soon as 100–110° C. is reached, 0.023 mol of sodium methylate, or 4.16 g of a 30% solution in methanol, is added. The methanol that emerges from the transamidification reaction is collected, and the heating is continued up to 130° C. for approximately 2 hours under reduced pressure to facilitate the removal of methanol.

The product that is thus produced is diluted at 50% by weight with the aromatic solvent fraction that is used in Example 1.

EXAMPLE 5

Into a stirred stainless steel reactor, with a 120-liter capacity, 65 kg of polymerized linseed oil with a viscosity of 10 Pa.s at 20° C. and 35 kg of diethanolamine are introduced.

The mixture is heated up to 160° C. under a nitrogen atmosphere. The target temperature is reached after 80 minutes, and this temperature of 160° C. is held for about 100 minutes.

The product that is obtained is diluted after cooling to 120° C. in a stirred tank that holds 100 kg of ricin oil methyl ester to obtain a dilution by weight of 50%.

The composition of the product that is produced before dilution, determined by assay, is as follows:

1.39 mol/kg of total amine,
1.3 mol/kg of free diethanolamine,
0.09 mol/kg of amino-esters,
0.6 mol/kg of free glycerine,
0.12 mol/kg of monoglycerides,
on the order of 0.17 mol/kg of diethanolamine fatty acid salts, and
1.8 mol/kg of fatty acid amides.

The viscosity at 20° C. of the product before dilution is 12.710 Pa.s, and after dilution at 50/50 by weight in ricin methyl ester, the viscosity at 20° C. is 0.567 Pa.s.

EXAMPLE 6

With a bar magnet, 0.15 g of emulsifying solution that is produced in Example 1 (product diluted at 50% with an aromatic fraction) is dissolved with 90 g of a hydrocarbon mixture that represents a petroleum condensate.

The composition by weight of the condensate is as follows:

for the molecules that have less than 11 carbon atoms:
  20% paraffins and isoparaffins, 48% naphthenes, 10% aromatic compounds; and
for the molecules that have at least 11 carbon atoms:
  22% of a mixture of paraffins, isoparaffins, naphthenes and aromatic compounds.

After 10 to 15 minutes of continuous stirring, 10 g of water is added to this mixture, and it is stirred with a turbine-type stirring mechanism at 8000 rpm for 30 seconds. The emulsion that is formed is fine and stable. It is of the water-in-oil type.

EXAMPLE 7

0.3 g of emulsifying solution that is produced in Example 5 (product diluted 50% by weight with ricin methyl ester) is dissolved in 180 g of water, then 20 g of refined colza oil is added, and stirring is done at 8000 rpm for 30 seconds with a turbine-type stirring mechanism. The emulsion that is formed is fine and stable. It is of the oil-in-water type.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope of thereof, can make various changes or modifications of the invention to adapt it to various usages and conditions.

What is claimed is:

1. A composition comprising a mixture of amides, amines, ester-amides, ester-amines, amine salts, and monoglycerides, all derived from monomeric, dimeric, trimeric, and tetrameric fatty acids reacted with at least one amino alcohol.

2. A composition according to claim 1, further comprising at least one solvent.

3. A composition according to claim 2, wherein said solvent is an aromatic solvent; a monoalcohol, a diol, or an ester of a C1 to C4 monoalcohol and a C6 to C22 fatty acid.

4. A composition according to claim 1, produced by a process comprising subjecting a thermally polymerized polyunsaturated vegetable oil to transamidification, with excess amino alcohol, optionally in the presence of catalyst.

5. A composition according to claim 4, wherein the polymerized vegetable oil has a viscosity of 5 to 65 Pa.s at 20° C.

6. A composition according to claim 5, wherein the initial vegetable oil is linseed oil.

7. A composition according to claim 4, wherein the molar ratio of the amino alcohol to the polymerized oil is 3 to 6.

8. A composition according to claim 4, wherein the amino alcohol is diethanolamine.

9. A composition according to claim 4, wherein the transamidification is conducted at a temperature of 100 to 200° C.

10. A composition according to claim 9, wherein the transamidification is conducted for 15 to 200 minutes.

11. In a method of forming an oil-in-water or water-in-oil emulsion with an emulsifying agent, the improvement comprising using a composition according to claim 1 as the emulsifying agent.

12. In a method of forming a stable ice dispersion in a light petroleum condensate, the improvement comprising adding to the light petroleum condensate containing dispersed petroleum of ice, a stabilizing amount of a composition according to claim 1.

13. In a method of stabilizing a foam, the improvement comprising adding to the foam a stabilizing amount of composition according to claim 1.

14. A process for production of a composition comprising a mixture of amides, amines, ester-amides, ester-amines, amine salts, and monoglycerides, comprising subjecting a polymerized polyunsaturated vegetable oil to transamidification, with excess amino alcohol, optionally in the presence of catalyst.

15. A process according to claim 14, wherein the polymerized vegetable oil is obtained by polymerization of a vegetable oil with a high content of polyunsaturated acids, such that it has a viscosity of 5 to 65 Pa.s at 20° C.

16. A process according to claim 15, wherein the initial vegetable oil is linseed oil.

17. A process according to claim 14, wherein the molar ratio of the amino alcohol to the polymerized oil is 3 to 6.

18. A process according to claim 17, wherein the molar ratio is 4.5.

19. A process according to claim 14, wherein the amino alcohol that is used is diethanolamine.

20. A process according to claim 14, wherein the transamidification is obtained with a catalyst, after a heating time of 15 to 200 minutes.

21. A process according to claim 20, wherein the heating time is about 80 to 120.

22. A process according to claim 14, wherein the reaction temperature is 100 to 200° C.

23. A process according to claim 22, wherein the reaction temperature is about 160° C.

24. A process according to claim 14 wherein the transamidification is obtained without a catalyst, after a heating time of 15 to 200 minutes.

25. A process according to claim 24, wherein the reaction temperature is about 160° C.

* * * * *